US009206436B2

(12) United States Patent
Chen et al.

(10) Patent No.: US 9,206,436 B2
(45) Date of Patent: Dec. 8, 2015

(54) KEY GENE REGULATING CELL WALL BIOSYNTHESIS AND RECALCITRANCE IN *POPULUS*, GENE Y

(71) Applicant: UT BATTELLE, LLC, Oak Ridge, TN (US)

(72) Inventors: Jay Chen, Oak Ridge, TN (US); Nancy L. Engle, Oak Ridge, TN (US); Lee E. Gunter, Oak Ridge, TN (US); Sara Jawdy, Oak Ridge, TN (US); Timothy J. Tschaplinski, Oak Ridge, TN (US); Gerald A. Tuskan, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 33 days.

(21) Appl. No.: 14/136,485

(22) Filed: Dec. 20, 2013

(65) Prior Publication Data
US 2014/0182013 A1  Jun. 26, 2014

Related U.S. Application Data

(60) Provisional application No. 61/740,068, filed on Dec. 20, 2012.

(51) Int. Cl.
*C12N 9/10* (2006.01)
*C12N 15/82* (2006.01)

(52) U.S. Cl.
CPC .......... *C12N 15/8255* (2013.01); *C12N 9/1029* (2013.01); *C12N 15/8218* (2013.01)

(58) Field of Classification Search
None
See application file for complete search history.

(56) References Cited

U.S. PATENT DOCUMENTS

| | | | | |
|---|---|---|---|---|
| 5,558,071 | A * | 9/1996 | Ward et al. | 123/598 |
| 5,702,933 | A * | 12/1997 | Klee et al. | 800/283 |
| 5,959,178 | A * | 9/1999 | Fritig et al. | 800/298 |
| 6,441,272 | B1 * | 8/2002 | Ye | 800/278 |
| 8,461,129 | B2 * | 6/2013 | Bolduc et al. | 514/54 |
| 2004/0146904 | A1 * | 7/2004 | Phillips et al. | 435/6 |
| 2011/0028412 | A1 * | 2/2011 | Cappello et al. | 514/25 |
| 2013/0041004 | A1 * | 2/2013 | Drager et al. | 514/394 |
| 2013/0084243 | A1 * | 4/2013 | Goetsch et al. | 424/1.49 |
| 2013/0096073 | A1 * | 4/2013 | Sidelman | 514/21.6 |

OTHER PUBLICATIONS

Tuskan et al, Science (2006) vol. 313 pp. 1596-1604.*
Colliver et al., PMB (1997) vol. 35, pp. 509-522.*
Stanton et al , S. Jansson et al. (eds.), Genetics and Genomics of Populus, Plant Genetics and Genomics: Crops and Models 8, (2010) pp. 309-347.*
Elomaa et al. (1996) Molecular Breeding, vol. 2, pp. 41-50.*

* cited by examiner

*Primary Examiner* — Amjad Abraham
*Assistant Examiner* — Ryan H Brown
(74) *Attorney, Agent, or Firm* — Scully, Scott, Murphy & Presser, P.C.

(57) ABSTRACT

This disclosure provides methods and transgenic plants for improved production of renewable biofuels and other plant-derived biomaterials by altering the expression and/or activity of Gene Y, an O-acetyltransferase. This disclosure also provides expression vectors containing a nucleic acid (Gene Y) which encodes the polypeptide of SEQ ID NO: 1 and is operably linked to a heterologous promoter.

9 Claims, 4 Drawing Sheets

A

B

KEY GENE REGULATING CELL WALL BIOSYNTHESIS AND RECALCITRANCE IN *POPULUS*, GENE Y

CROSS-REFERENCE TO RELATED APPLICATIONS

This application claims priority to U.S. provisional application 61/740,068, filed Dec. 20, 2012, which is incorporated herein in its entirety.

STATEMENT REGARDING FEDERALLY SPONSORED RESEARCH OR DEVELOPMENT

This disclosure was made with government support under a research project supported by under Contract No. DE-AC05-00OR22725 awarded by the U.S. Department of Energy. The government has certain rights in this disclosure.

INCORPORATION BY REFERENCE OF SEQUENCE LISTING

The Sequence Listing in the ASCII text file, named as 29275 SEQ.txt of 8 KB, created on Dec. 18, 2013, and submitted to the United States Patent and Trademark Office via EFS-Web, is incorporated herein by reference.

BACKGROUND OF THE DISCLOSURE

A major obstacle for the cost-effective production of renewable transportation fuels from lignocellulosic plant biomass is the difficulty of extracting sugars from the plant cell wall. Simple sugars are converted to fuel through degradation and saccharification of the obstinate plant cell walls and fermentation of these sugars to produce ethanol and other valuable products. Overcoming plant recalcitrance to releasing biomaterials bound in the cell wall is therefore an issue of primary importance in the development of biofuel technology.

Lignins, complex interlinking biopolymers derived from hydroxyphenylpropanoids, provide rigidity and structure to plant cell walls for plant growth and transport of water and nutrients, and are significant contributors to plant recalcitrance. Lignins are composed primarily of syringyl (S), guaiacyl (G) and p-hydroxyphenyl (H) monolignol subunits, which are derived from sinapyl, coniferyl and p-coumaryl alcohols, respectively. The subunit ratio and resulting structure of plant lignins varies according to the genotype, environment, tissue type and maturity of the plant and as such, lignins are very heterogeneous and can vary significantly between different plants, within different tissues of a single plant and even within a single plant cell (Simmons B A et al., *Curr Opin Plant Biol.* 13:313-20 (2010)). This complexity and heterogeneity hinders the development of conversion technology able to process a range of sustainable feedstocks in a cost-effective manner. Identification and manipulation of genes regulating cell wall biosynthesis and recalcitrance is one of the critical steps for overcoming such constraints related to efficient production of cellulosic sugars and ethanol using plant biomass.

BRIEF SUMMARY OF THE DISCLOSURE

This disclosure provides methods and transgenic plants for improved production of renewable fuels and other plant-derived biomaterials by altering the expression and/or activity of Gene Y, an O-acetyltransferase.

DETAILED DESCRIPTION OF THE DISCLOSURE

Figures 1A, 1B:
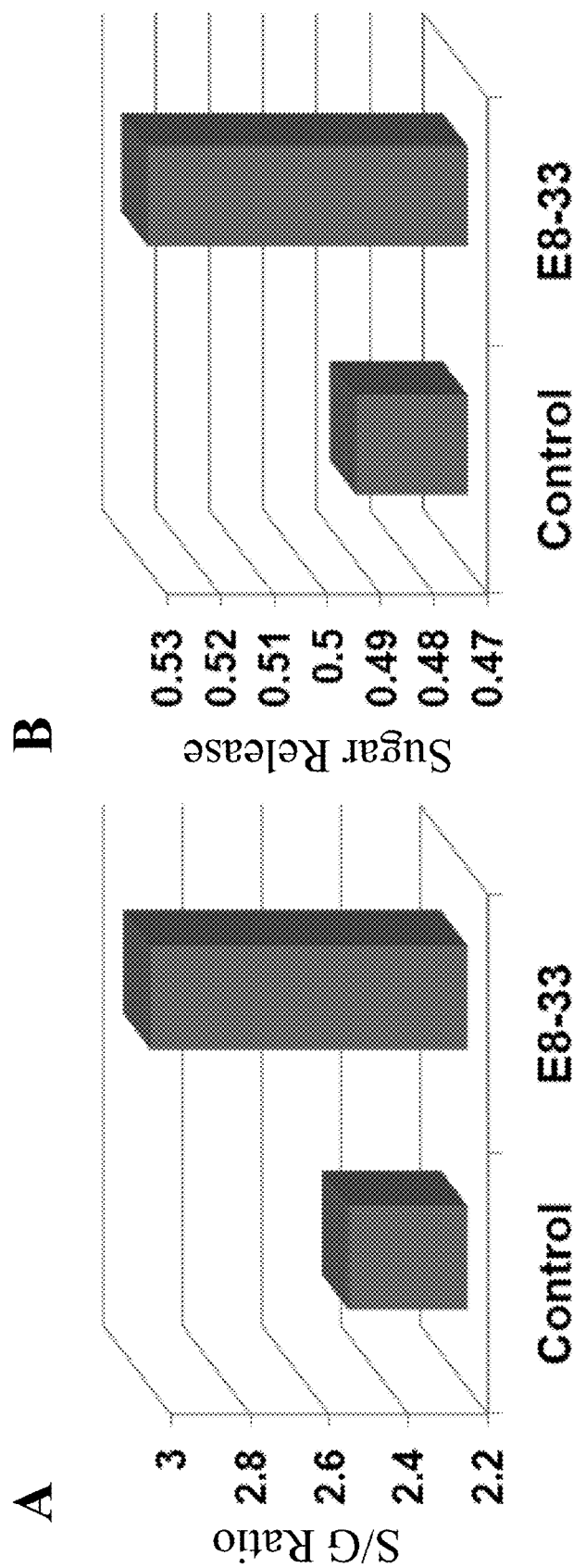
FIGS. 1A-1B. *Populus* activation tagged line E8-33 displays (A) higher S/G lignin ratio and (B) increased total sugar release.

Production of renewable fuel from lignocellulosic plant biomass is based on extraction of sugars from plant cell wall material. This extraction process is hampered by the presence of lignin in the cell wall. Lignins contribute to plant "recalcitrance", a term referring to the inherent resistance of plant material to release polysaccharides and other desirable biomaterials from an interwoven matrix of desirable and undesirable materials. Lignins are difficult to break down by physical, chemical and other methods and processing plant materials to release sugars from lignins requires extensive thermochemical treatment. In addition, lignin processing creates inhibitory byproducts, such as acetylated compounds, that hamper further extraction and fermentation. Acetyl esters released during treatment of cell wall polymers can inhibit saccharification of biomass. The released acetate is also inhibitory to the organisms used to ferment the sugars into useful byproducts.

Gene Y (Populus gene model POPTR_0010s15840) has been identified by the present inventors as an important regulator of plant cell wall biosynthesis and biomass recalcitrance. Gene Y has been found to modulate lignin composition, specifically the ratio of syringyl (S) to guaiacyl (G) monolignol subunits, referred to herein as the "S/G ratio" or "S:G ratio", of lignin biopolymers. Manipulation of the expression level of this gene in plants alters the S/G ratio, which affects cell wall chemistry and the rate of sugar release. This facilitates more efficient conversion of biomass to sugar monomers during the fermentation process, leading to an increase in cellulosic ethanol production and a reduction in biofuel production cost. In accordance with these findings by the inventors, methods for modulating Gene Y to increase or decrease the ratio of S to G subunits are provided, as well as Gene Y related polypeptides, expression vectors and transgenic plants, are provided and disclosed herein in detail.

Gene Y Homologs and Encoded Polypeptides

In one aspect, this disclosure is directed to an isolated polypeptide encoded by Gene Y or homologs thereof. Gene Y encodes a polypeptide of SEQ ID NO:1. This polypeptide is identified as an O-acetyltransferase. An O-acetyltransferase catalyzes the transfer of an acetyl group onto an oxygen moiety of a target molecule. Without being bound, the Gene Y O-acetyltransferase is believed to catalyze the acetylation of cell wall polysaccharides, and may further acetylate lignin biosynthetic pathway components and lignins themselves. Increases or decreases in acetylated plant cell wall components can be determined, for example, by nuclear magnetic resonance (NMR) spectroscopy.

This disclosure also provides homologs of the polypeptide encoded by Gene Y. A Gene Y homolog can be a homolog ortholog or variant of the polypeptide having the amino acid sequence set forth in SEQ ID NO:1. For example, a Gene Y homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO:1.

In some embodiments, a homolog of SEQ ID NO:1 is a functional homolog. A functional homolog is a polypeptide that has sequence similarity to SEQ ID NO:1 and that carries out one or more of the biochemical or physiological function(s) of the polypeptide of SEQ ID NO:1. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

A homolog of the polypeptide encoded by Gene Y can be a native Gene Y protein, i.e., one or more additional copies of the coding sequence for a Gene Y homolog that is naturally present in the cell. Alternatively, a homolog of the polypeptide encoded by Gene Y can be heterologous to the cell, e.g., a transgenic *Populus* plant can contain the coding sequence for a Gene Y homolog from an *Arabidopsis* plant, for example.

Cell Wall Modulation

In a further aspect, this disclosure provides methods for cell wall modulation by increasing or decreasing expression of Gene Y or a Gene Y homolog in a plant or plant cell. Nucleic acid constructs which are employed in these methods are described herein below. Transgenic plants and plant cells in which expression of Gene Y or a Gene Y homolog is increased or decreased are also described below.

By "cell wall modulation" is meant that one or more cell wall-related phenotypes is altered in a transgenic plant, plant cell or plant tissue relative to cell-wall phenotypes in a wild-type or control plant without the transgene. Cell wall modulation can include any alteration in one or more of: plant recalcitrance; lignin biosynthesis; amount of lignin; composition of lignin, such as S/G ratio, S/H ratio, G/H ratio or incorporation of phenolic components other than S, G or H monolignols into lignin; lignin subunit crosslinking; cell wall thickness; cell wall degradability; amount or composition of cellulose or hemicellulose; amount or composition of polysaccharides; and acetylation of one or more cell wall compounds, such as acetylation of saccharides or other components of the lignin biosynthetic pathway.

The composition and structure of lignin can be characterized by GC-MS, LC-MS, NMR spectroscopy, Fourier-transform infrared spectroscopy and/or other known techniques.

In addition, histochemical analysis can be performed to determine the amount and distribution of lignin in a plant. For example, tissue sections can be stained with toluidine blue O (TBO), the Wiesner reagent or the Maiule reagent. TBO is a metachromatic stain that imparts a turquoise color to lignified cell walls and stains non-lignified cell walls purple. Phloroglucinol stains lignified cells red upon reaction with hydroxycinnamaldehyde groups present in the polymer. The Maule reagent is a histochemical stain that allows syringyl lignin to be distinguished chromogenically from guaiacyl lignin in situ. A pink or red color can indicate the presence of syringyl units, whereas a light to dark brown color can indicate the presence of guaiacyl units.

By manipulating the expression of Gene Y or a Gene Y homolog, the amount and/or rate of S subunit to G subunit biosynthesis or the incorporation of S to G subunits into the lignin structure, can be modulated. Alteration in the S/G subunit ratio alters the lignin composition of the plant cell wall. Manipulating the expression of Gene Y or a Gene Y homolog can thus modulate the lignin composition of a plant. For example, the lignin composition can be altered from essentially 50% syringyl ("S"):50% guaiacyl ("G") units to essentially 100% syringyl units, or essentially 100% guaiacyl units. The terms "units" and "subunits" are used interchangeably herein.

In some embodiments, the method disclosed herein (i.e., by manipulating expression of Gene Y and/or a Gene Y homolog) results in an S/G ratio in a plant (e.g., *Populus* species), for example, of greater than 2:1, e.g., 2.1:1, 2.2:1, 2.5:1, 2.8:1, 3.0:1, 3.5:1, 4:1, etc or less than 2:1, e.g., 0.5:1, 0.8:1, 1:1, 1.2:1, 1.5:1, 1.8:1, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant (i.e., without the manipulation of expression of Gene Y and/or a Gene Y homolog). In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

In conjunction with the present invention, the S/G ratio can be increased or decreased in a plant by increasing or decreasing one or more compounds in a lignin biosynthesis pathway. In certain cases, the amount of more than one compound (e.g., two, three, four, five, six, seven, eight, nine, ten or even more compounds) included in a lignin biosynthetic pathway can be modulated relative to a control plant, tissue or cell that is not transgenic for a lignin-modulating polypeptide described herein. Such a compound can be, for example, a precursor compound, an intermediate compound or an end product in a lignin biosynthesis pathway. Modification of the biosynthetic pathway can alter the S/G ratio and can also reduce the total lignin content, either or both of which can decrease recalcitrance.

Compounds and enzymes in the lignin biosynthesis pathway include, for example, phenylalanine, phenylalanine ammonia lyase (PAL), cinnamic acid, cinnamate 4-hydroxylase (C4H), p-coumaric acid, p-coumaraldehyde, p-coumaryl alcohol, caffeic acid, ferulic acid, 5-hydroxy-ferulic acid, 5-hydroxy-feruloyl CoA, sinapic acid, sinapoyl CoA, p-coumaroyl CoA, p-coumaroyl shikimic acid, p-coumaroyl quinic acid, caffeoyl shikimic acid, caffeoyl quinic acid, caffeoyl CoA, feruloyl CoA, coniferaldehyde, 5-hydroxy-coniferaldehyde, sinapaldehyde, coniferyl alcohol, 5-hydroxy-coniferyl alcohol, sinapyl alcohol, caffeyl aldehyde and caffeoyl alcohol.

Down-regulating expression of the PAL and CCoAOMT genes, for example, increases the S/G ratio in tobacco and alfalfa, respectively, while down-regulating expression of the C4H, F5H, COMT and CAD genes decreases the S/G ratio in alfalfa (Li, et al., Plant J. 54:569-581, 2008). Each of these alterations in expression also leads to a decrease in total lignin content and a reduction in recalcitrance (Id.).

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in Populus at values above 2.0. The exact way this occurs is not known though it is speculated that lignin remains intact during saccharification under high temperature and/or pressure. Nevertheless, biomass with S/G ratio above 2.0 releases more sugar.

Expression of Gene Y or a Gene Y homolog can be utilized to increase the S/G ratio in a plant. One mechanism for this altered ratio is an increase in acetylation of a component or components of the lignin biosynthetic pathway. Increased Gene Y homolog O-acetyltransferase activity can also alter precursors in the polysaccharide biosynthetic pathway, leading to increased acetylation of hemicellulose, which is associated with increased sugar release. Sugar release refers to the amount of 5- and 6-carbon sugars that can be recovered from a plant using standard techniques to extract these sugars from plant materials. The greater the acetylation of cell wall sugars, the lower the degree of crosslinking of the cell wall polymers, and hence, the greater ease of cell wall breakdown and sugar release during bioprocessing. Sugar release can be measured as g sugar released per g of biomass (raw plant material). Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose. Thus, overexpression of a Gene Y homolog can reduce recalcitrance and improve sugar release.

The amount of S units can be increased by increasing expression of Gene Y or a Gene Y homolog. Increased expression can be achieved, for example, by insertion of an enhancer element, such as described in the Example, into the endogenous Gene Y homolog promoter region. Insertion of a T-DNA enhancer element into the Gene Y homolog promoter, for example, results in an S/G ratio in Populus of about 3.0. Gene Y homolog overexpression can also be achieved by expressing the Gene Y homolog under the control of one or more promoters, as described in detail below. Such promoters can be constitutive or inducible. Such promoters can be broadly expressing or tissue-specific. Overexpression of a Gene Y homolog can also be achieved by expression of multiple copies of the Gene Y homolog, resulting in increased production of the Gene Y homolog expression product.

To further increase the S/G ratio, for example to achieve an S/G ratio greater than 3:1, Gene Y homolog overexpression can be coupled with decreased expression of, for example, the PAL and CCoAOMT genes. Increased expression of a Gene Y homolog, alone or in combination with other modifications, such as decreasing expression or activity of additional components of the lignin biosynthetic pathway such as the PAL and/or CCoAOMT genes or a PAL and/or CCoAOMT homolog, can increase the S/G ratio of a plant by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a transgenic plant, plant tissue or plant cell provided herein as compared to the corresponding S/G ratio in a control plant. Similarly, increased expression of a Gene Y homolog, alone or in combination with such modifications, can increase the S/G ratio of a plant by 5%, 10%, 15%, 20%, 25%, 30%, 35%, 40%, 45%, 50%, 60%, 70%, 80%, 90%, 100% or more than 100%, in a transgenic plant, plant tissue or plant cell provided herein as compared to the corresponding S/G ratio in a control plant. The S/G ratio in transgenic Populus, for example, can be 2.1:1, 2.2:1, 2.5:1, 2.8:1, 3.0:1, 3.5:1, 4:1 or greater.

Expression of Gene Y or a Gene Y homolog can also be utilized to decrease the S/G ratio in a plant. Increasing the amount of G subunits increases subunits available for cross-linking, as noted above, but increased cross-linking creates a thinner cell wall that is also more degradable, which again decreases recalcitrance and increases sugar release Inhibition of a Gene Y homolog decreases the S/G ratio to below 2:1, which leads to a thinner, more degradable cell wall Inhibition of Gene Y homolog O-acetyltransferase activity also causes a decrease in acetylated products, thus reducing inhibitory byproducts during the fermentation process and improving biofuel production.

The S/G ratio can be decreased below 2:1 by inhibiting expression of a Gene Y homolog. Such inhibition can be achieved, for example, by nucleic acid based inhibition of the Gene Y homolog transcript, such as with RNAi inhibitory molecules as described in detail below. The S/G ratio can also be decreased by inhibiting expression of the C4H, F5H, COMT and/or CAD genes. The S/G ratio can be decreased further by inhibition of Gene Y homolog transcription products in combination with further modifications, such as inhibiting expression or activity of one or more components of the lignin biosynthetic pathway, for example inhibiting the C4H, F5H, COMT and/or CAD genes or a C4H, F5H, COMT and/or CAD homolog.

Decreasing expression of a Gene Y homolog, alone or in combination with other modifications, such as decreasing expression or activity of additional components of the lignin biosynthetic pathway such as the C4H, F5H, COMT and/or CAD genes or a C4H, F5H, COMT and/or CAD homolog, can decrease the S/G ratio of a plant by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a transgenic plant, plant tissue or plant cell provided herein as compared to the corresponding S/G ratio in a control plant. Similarly, decreased expression of a Gene Y homolog, alone or in combination with such modifications, can increase the S/G ratio of a plant by 5%, 10%, 15%, 20%, 25%, 30%, 35%, 40%, 45%, 50%, 60%, 70%, 80%, 90%, 100% or more than 100%, in a transgenic plant, plant tissue or plant cell provided herein as compared to the corresponding S/G ratio in a control plant. The S/G ratio in transgenic Populus, for example, can be 0.5:1, 0.8:1, 1:1, 1.2:1, 1.5:1, 1.8:1 or less than 0.5:1.

The composition of lignin can be also altered in a plant by having other phenolic compounds incorporated into lignin that are not S, G or H monolignols and are not normally incorporated into lignin in a wild-type plant. Such compounds can include, without limitation, dihydroconiferyl alcohol, coniferaldehyde, sinaplyaldehyde, hydroxycinnamaldehydes and hydroxybenzaldehydes. Incorporation of these compounds can alter lignin chemistry, make the cell wall more susceptible to degradation, reduce recalcitrance and improve production. Increased incorporation of these compounds into lignin can occur with modifications to the lignin biosynthetic pathway, such as by downregulating the CAD gene (Li, et al., *Plant J.* 54:569-581, 2008). Such modified expression patterns can be combined with up-regulation or down-regulation of a Gene Y homolog, as described above, to create transgenic plants, tissues or cells with lignin composition alterations both in S/G ratio and in integration of atypical phenolic monomers, to further reduce plant recalcitrance.

Expression Vectors and Other Nucleic Acids

This disclosure provides methods of modulating the lignin composition, i.e. S/G ratio and sugar release in a plant, comprising introducing into a plant cell an exogenous nucleic acid comprising a regulatory region operably linked to a nucleic acid encoding a Gene Y homolog where a tissue of a plant produced from the plant cell has a modulated cell wall compared to the cell wall in tissue of a control plant that does not comprise the nucleic acid.

This disclosure further provides methods of modulating the lignin composition, i.e. S/G ratio and sugar release in a plant, comprising introducing into a plant cell an exogenous nucleic acid comprising a regulatory region operably linked to a polynucleotide that is transcribed into an interfering RNA effective for inhibiting expression of a Gene Y homolog, where a tissue of a plant produced from the plant cell has a modulated cell wall compared to the cell wall in tissue of a control plant that does not comprise the nucleic acid.

Techniques for introducing nucleic acids into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., Plant Cell Rep. V19:304-310 (2000); Chang and Yang, Bot. Bull. Acad. Sin., V37:35-40 (1996) and Han et al., Biotechnology in Agriculture and Forestry, V44:291 (ed. by Y. P. S. Bajaj), Springer-Vernag, (1999).

A population of transgenic plants can be screened and/or selected for those members of the population that have a desired trait or phenotype conferred by expression of the transgene. Selection and/or screening can be carried out over one or more generations, which can be useful to identify those plants that have a desired trait, such as reduced recalcitrance; lignin modifications such as altered S/G ratio, S/H ratio, G/H ratio or incorporation of phenolic components other than S, G or H monolignols into lignin; modified amount or composition of cellulose or hemicellulose; modified amount or composition of polysaccharides; and modified acetylation of one or more cell wall compounds. Selection and/or screening can be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is exhibited by the plant.

The disclosure provides vectors and nucleic acid constructs for increasing or decreasing expression of a Gene Y homolog and other cell wall-modulating polypeptides, in a plant, plant tissue or plant cell.

Specific manipulation of the expression of Gene Y can be achieved through overexpression (i.e., via constitutive promoter) and under-expression (ie, via RNAi knockdown) approaches. When desirable, inducible promoters and tissue-specific promoters can also be used to drive the expression of this gene under particular conditions or in a specific tissue. Furthermore, this gene can potentially used as a marker in a breeding program for selection of favorable traits related to biomass recalcitrance. For example, individual nucleotide variants for Gene Y can be used in breeding programs to select parents for crossing and progeny for field testing via marker aided selection methods.

Vectors containing nucleic acids such as those described herein are provided. A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

As used herein, the term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., The Plant Cell, 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

Some suitable regulatory regions initiate transcription only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well. Methods for identifying and characterizing regulatory regions in plant genomic DNA include, for example, those described in the following references: Jordano et al., Plant Cell, 1:855-866 (1989); Bustos et al., Plant Cell, 1:839-854 (1989); Green et al., EMBO J., 7:4035-4044 (1988); Meier et al., Plant Cell, 3:309-316 (1991); and Zhang et al., Plant Physiology, 110: 1069-1079 (1996).

A promoter can be said to be "broadly expressing" when it promotes transcription in many, but not necessarily all, plant tissues. For example, a broadly expressing promoter can promote transcription of an operably linked sequence in one or more of the shoot, shoot tip (apex) and leaves, but weakly or not at all in tissues such as roots. As another example, a broadly expressing promoter can promote transcription of an operably linked sequence in one or more of the stem, shoot, shoot tip (apex) and leaves, but can promote transcription weakly or not at all in tissues such as reproductive tissues of flowers and developing seeds. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of Agrobacterium tumefaciens, the figwort mosaic virus 34S promoter, actin promoters such as the rice actin promoter and ubiquitin promoters such as the maize ubiquitin-1 promoter. In some cases, the CaMV 35S promoter is excluded from the category of broadly expressing promoters.

Root-active promoters confer transcription in root tissue, e.g., root endodermis, root epidermis or root vascular tissues. In some embodiments, root-active promoters are root-preferential promoters, i.e., confer transcription only or predominantly in root tissue. Root-preferential promoters include the root-specific subdomains of the CaMV 35S promoter (Lam et al., Proc. Natl. Acad. Sci. USA, 86:7890-7894 (1989)), root cell specific promoters reported by Conkling et al., Plant Physiol., 93:1203-1211 (1990) and the tobacco RD2 promoter.

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (Larix laricina), the pine cab6 promoter (Yamamoto et al., Plant Cell Physiol., 35:773-778 (1994)), the Cab-1 promoter from wheat (Fejes et al., Plant Mol. Biol., 15:921-932 (1990)), the CAB-1 promoter from spinach (Lubberstedt et al., Plant Physiol., 104: 997-1006 (1994)), the cab IR promoter from rice (Luan et al., Plant Cell, 4:971-981 (1992)), the pyruvate orthophosphate dikinase (PPDK) promoter from corn (Matsuoka et al., Proc. Natl. Acad. Sci. USA, 90:9586-9590 (1993)), the tobacco Lhcb1*2 promoter (Cerdan et al., Plant Mol. Biol., 33:245-255 (1997)), the Arabidopsis SUC2 sucrose-H+ symporter promoter (Truernit et al., Planta, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Such enzymes include, without limitation, 4-(hydroxy)cinnamoyl CoA ligase (EC 6.2.1.12), ferulate 5-hydroxylase, cinnamoyl CoA reductase (EC 1.2.1.44), cinnamate 4-hydroxylase (EC 1.14.13.11) and cinnamyl alcohol dehydrogenase (EC 1.1.1.195). Examples of lignin biosynthesis promoters include promoters of the switchgrass (Panicum virgatum), rice (Oryza sativa), corn (Zea mays) and wheat (Triticum aestivum) homologs of the Populus cinnamate 4-hydroxylase, caffeoyl-CoA O-methyltransferase and caffeic acid O-methyltransferase genes. Also suitable are promoters of Arabidopsis genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, Plant Cell, 3(10):1051-1061 (1991)), the Commelina yellow mottle virus (CoYMV) promoter (Medberry et al., Plant Cell, 4(2): 185-192 (1992)) and the rice tungro bacilliform virus (RTBV) promoter (Dai et al., Proc. Natl. Acad. Sci. USA, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters.

Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

The polynucleotides and recombinant vectors described herein can be used to express or inhibit expression of a Gene Y homolog. The term "expression" refers to the process of converting genetic information of a polynucleotide into RNA through transcription, which is catalyzed by an enzyme, RNA polymerase and into protein, through translation of mRNA on ribosomes. "Up-regulation" or "overexpression" or "activation" refers to regulation that increases the production of expression products (mRNA, polypeptide or both) relative to basal or native states, while "inhibition" or "down-regulation" or "repression" refers to regulation that decreases production of expression products (mRNA, polypeptide or both) relative to basal or native states.

A "Gene Y homolog inhibitor" is a substance that can reduce or prevent expression or activity of a Gene Y homolog. For example, an inhibitor of expression of a Gene Y homolog can reduce or eliminate transcription and/or translation of the Gene Y gene product, thus reducing Gene Y protein expression.

A modulated level of gene expression refers to a comparison of the level of expression of a transcript of a gene or the amount of its corresponding polypeptide in the presence and absence of a Gene Y homolog described herein and refers to a measurable or observable change in the level of expression of a transcript of a gene or the amount of its corresponding polypeptide relative to a control plant or plant cell under the same conditions (e.g., as measured through a suitable assay such as quantitative RT-PCR, a Northern blot, a Western blot or through an observable change in phenotype, chemical profile or metabolic profile). A modulated level of gene expression can include up-regulated or down-regulated expression of a transcript of a gene or polypeptide relative to a control plant or plant cell under the same conditions. Modulated expression levels can occur under different environmental or developmental conditions or in different locations than those exhibited by a plant or plant cell in its native state.

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit Gene Y expression in plants. Suitable inhibitors include full-length nucleic acids encoding a Gene Y homolog or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo, see, Perriman et al., Proc. Natl. Acad. Sci. USA, 92(13): 6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in Tetrahymena thermophila, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides or from 25 nucleotides to 200 nucleotides. The loop portion of the RNA can include an intron or a fragment thereof. A double stranded RNA can have zero, one, two, three, four, five, six, seven, eight, nine, ten or more stem-loop structures.

A construct including a sequence that is operably linked to a regulatory region and a transcription termination sequence and that is transcribed into an RNA that can form a double stranded RNA, is transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

Constructs containing regulatory regions operably linked to nucleic acid molecules in sense orientation can also be used to inhibit the expression of a gene. The transcription product can be similar or identical to the sense coding sequence of a polypeptide of interest. The transcription product can also be unpolyadenylated, lack a 5' cap structure or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30 or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides or from about 21 nucleotides to about 25 nucleotides.

The sense sequence complementary to the antisense sequence can be a sequence present within the mRNA of a cell wall-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different and the multiple antisense sequences can be identical or different. For example, a construct can have a nucleic acid having one strand that is a template for two identical sense sequences and two identical antisense sequences that are complementary to the two identical sense sequences.

Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., Plant Physiol., 141:1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length or from about 18 to about 25 nucleotides in length.

In some embodiments, a suitable nucleic acid can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, Antisense Nucleic Acid Drug Dev., 7:187-195; Hyrup et al., Bioorgan. Med. Chem., 4:5-23 (1996). In addition, the deoxyphosphate backbone can be replaced with, for example, a phosphorothioate or phosphorodithioate backbone, a phosphoroamidite or an alkyl phosphotriester backbone.

Transgenic Plants/Plant Species/Plant Cells

Provided herein are transgenic plants, plant tissues and plant cells comprising at least one recombinant nucleic acid construct or exogenous nucleic acid. A recombinant nucleic acid construct or exogenous nucleic acid can include a regulatory region as described herein, a nucleic acid encoding a Gene Y homolog or other cell wall modulating polypeptides as described herein or both. In certain cases, a transgenic plant cell or plant comprises at least two recombinant nucleic acid constructs or exogenous nucleic acids, e.g., one including a nucleic acid encoding a Gene Y homolog and another including a nucleic acid encoding a second Gene Y homolog or one or more different cell wall modulating polypeptides.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers, compounds in a lignin biosynthetic pathway or flavonoids. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous Gene Y homolog whose expression has not previously been confirmed in particular recipient cells.

Initial and immediate application of the manipulation of the expression of Gene Y can be made in the bioenergy crops *Populus* and switchgrass but the application can be extended to other bioenergy crops such as corn, other sources of lignocellulosic biomass and other model plants e.g., *Salix, Miscanthus,* rice and *Medicago.*

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus,* oat, rice, rye, ryegrass, sorghum, sudangrass, sugarcane, sweet corn, switchgrass, turf grasses, timothy and wheat. Gymnosperms such as fir, pine and spruce can also be suitable.

Thus, the methods and compositions described herein can be used with dicotyledonous plants belonging, for example, to the orders Asterales, Capparales, Euphorbiales, Fabales, Fagales, Juglandales, Lamiales, Linales, Malvales, Myrtales, Rosales, Salicales, Sapindales, Scrophulariales and Solanales. The methods and compositions described herein also can be utilized with monocotyledonous plants such as those belonging to the order Cyperales and with plants belonging to Gymnospermae, e.g., Cycadales, Ephedrales, Ginkgoales, Gnetales and Pinales.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans,*

*Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*.

In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*.

In certain embodiments, the polynucleotides and vectors described herein can be used to transform a number of monocotyledonous and dicotyledonous plants and plant cell systems, wherein such plants are hybrids of different species or varieties of a specific (e.g., *Saccharum* sp.×*Miscanthus* sp.)

In one aspect, a plant cell is provided. The plant cell comprises an endogenous or exogenous nucleic acid comprising a regulatory region operably linked to a polynucleotide encoding a Gene Y homolog where a tissue of a plant produced from the plant cell has a modulated cell wall compared to the cell wall in tissue of a control plant that does not comprise the nucleic acid.

The plant can be from a genus selected from the group consisting of Eucalyptus, *Hordeum, Medicago, Miscanthus oryza, Panicum, Pinus, Populus, Prunus, Quercus, Saccharum, Sorghum, Trifolium, Triticum* and *Zea*. The plant can be a species selected from *Miscanthus* hybrid (*Miscanthus×giganteus*), *Miscanthus sinensis, Miscanthus sacchariflorus, Panicum virgatum, Populus* spp. and *Saccharum* spp.

The cell can further comprise a nucleic acid encoding a second Gene Y homolog operably linked to a second regulatory region. The nucleic acid encoding a second Gene Y homolog operably linked to a second regulatory region can be present on a second recombinant nucleic acid construct. This allows expression of the Gene Y homolog in multiple combinations, such as under control of different promoters or multiple copies of the gene to further increase expression of the Gene Y homolog.

In another aspect, a plant cell comprising a Gene Y inhibitor is provided. The plant cell comprises an exogenous nucleic acid, the exogenous nucleic acid comprising a regulatory region operably linked to a polynucleotide that is transcribed into an interfering RNA effective for inhibiting expression of a Gene Y homolog where a tissue of a plant produced from the plant cell has a modulated cell wall compared to the cell wall in tissue of a control plant that does not comprise the nucleic acid. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have a modulated cell wall compared to the cell wall in tissue of a control plant that does not comprise the nucleic acid.

Articles of Manufacture

The materials and methods described herein are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as herbaceous and woody plants. Examples of biomass renewable energy source plants include: poplar, switchgrass, elephant grass, giant chinese silver grass, energycane, giant reed (also known as wild cane), *miscanthus*, tall fescue, bermuda grass, *sorghum, napiergrass* (also known as uganda grass), triticale, rye, winter wheat, shrub poplar, shrub willow, big bluestem, reed canary grass and corn.

Also, provided herein are transgenic plants, such as trees and grasses, having a modulated cell wall, which can be valuable for the production of biofuels and for increasing the yield of desirable materials from the plant material.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide increased amounts of lignin or altered S/G lignin ratio in one or more tissues of plants grown from such seeds.

The invention will be further described in the following examples, which do not limit the scope of the invention described in the claims.

EXAMPLE

An activation tagged hybrid *Populus* (*P. tremula×alba*) population (generated by transforming *Populus* with T-DNA containing enhancer tetramer) consisting of 463 independent transgenic lines was utilized. Core and cutting samples were harvested from each of these lines. The cores were dried in a 70° C. drying oven and then coarsely ground through 20 mesh sieve using a Wiley Mill. These samples were then barcoded and subjected to biomass characterization via molecular beam spectrometry (MBMS) and saccharification treatments. The phenotypic traits measured included lignin percentage, S/G ratio (ratio of syringyl to guaiacyl units), hemicellulose content, cellulose content, xylose release rate, glucose release rate and total sugar release rate. Plants displaying alterations in these cell wall-related phenotypes are referred to as having "extreme cell wall chemistry" or "extreme wood chemistry" phenotypes, defined as an alteration of cell wall-related phenotypes by a value of ±2.5 standard deviations away from the wild-type mean. Lines were selected that had values ±2.5 standard deviations away from the wild-type mean in any of the phenotypic traits. These lines were defined as lines with extreme wood chemistry phenotypes and 24 lines were so identified.

Metabolite profiling was performed as follows. Frozen tissues were shipped to ORNL, freeze dried, ground with a micro-Wiley mill with approximately 50 mg of sample tissue (fresh weight) were twice extracted with 2.5 mL 80% ethanol overnight and then combined prior to drying a 0.5-ml aliquot in a nitrogen stream. Sorbitol was added (to achieve 15 ng/μL injected) before extraction as an internal standard to correct for differences in extraction efficiency, subsequent differences in derivatization efficiency and changes in sample volume during heating. Dried extracts were dissolved in 500 μL of silylation—grade acetonitrile followed by the addition of 500 μL N-methyl-N-trimethylsilyltrifluoroacetamide (MSTFA) with 1% trimethylchlorosilane (TMCS) (Thermo Scientific, Bellefonte, Pa.), and samples then heated for 1 h at 70° C. to generate trimethylsilyl (TMS) derivatives (Tschaplinski et al., *Biotechnol. Biofuels* 5:71 (2012); Li et al., *Biotechnol. Biofuels* 5:2 (2012)). After 2 days, 1-μL aliquots were injected into an Agilent Technologies Inc. (Santa Clara, Calif.) 5975C inert XL gas chromatograph-mass spectrometer, fitted with an Rtx-5MS with Integra-guard (5% diphenyl/95% dimethyl polysiloxane) 30 m×250 μm×0.25 μm film thickness capillary column. The standard quadrupole GC-MS was operated in the electron impact (70 eV) ionization mode, targeting 6 full-spectrum (50-650 Da) scans per second. Gas (helium) flow was set at 1.0 mL per minute with the injection port configured in the splitless mode. The injection port, MS Source, and MS Quad temperatures were set to 250° C., 230° C., and 150° C., respectively. The initial oven temperature was held at 50° C. for 2 min and was programmed to increase at 20° C. per min to 325° C. and held for another 11 min, before cycling back to the initial conditions. Metabolite peaks were extracted using a key selected ion, characteristic m/z fragment, rather than the total ion chromatogram, to minimize integrating co-eluting metabolites. The extracted peaks of known metabolites were scaled back up to the total ion current using predetermined scaling factors. Peaks were quantified by area integration and the concentrations were normalized to the quantity of the internal standard (sorbitol) recovered, amount of sample extracted, derivatized, and injected. A large user-created database (>1900 spectra) of mass spectral electron impact ionization (EI) fragmentation patterns of TMS-derivatized compounds, as well as the Wiley Registry 8th Edition combined with NIST 05 mass spectral database, were used to identify the metabolites of interest to be quantified.

These lines were subjected to the following additional analysis: (1) Thermal Asymmetric Interlaced PCR (TAIL-PCR) analysis to determine the T-DNA insertion site(s) and to identify candidate genes, (2) Quantitative RT-PCR (qRT) to validate the activation of candidate genes and (3) Gas chromatography-mass spectrometry (GC-MS)-based metabolomic profiling to determine the impact of gene up-regulation on secondary and small molecules. On the basis of these analyses, 6 lines were selected for further characterization.

The *Populus* activation tagged line E8-33 displayed high S/G ratio and was one of those 24 lines with extreme wood chemistry phenotypes. The S/G ratio in E8-33 was at 3.0, significantly higher than that in control plants, which averaged an S/G ratio of 2.6 (FIG. 1A). This resulted in an approximate 10% increase in total sugar release, with E8-33 lines releasing 0.53 g combined glucose and xylose per gram of biomass raw material, compared with control plants, which released 0.49 g combined glucose and xylose per gram of biomass raw material (FIG. 1B).

Figure 2:
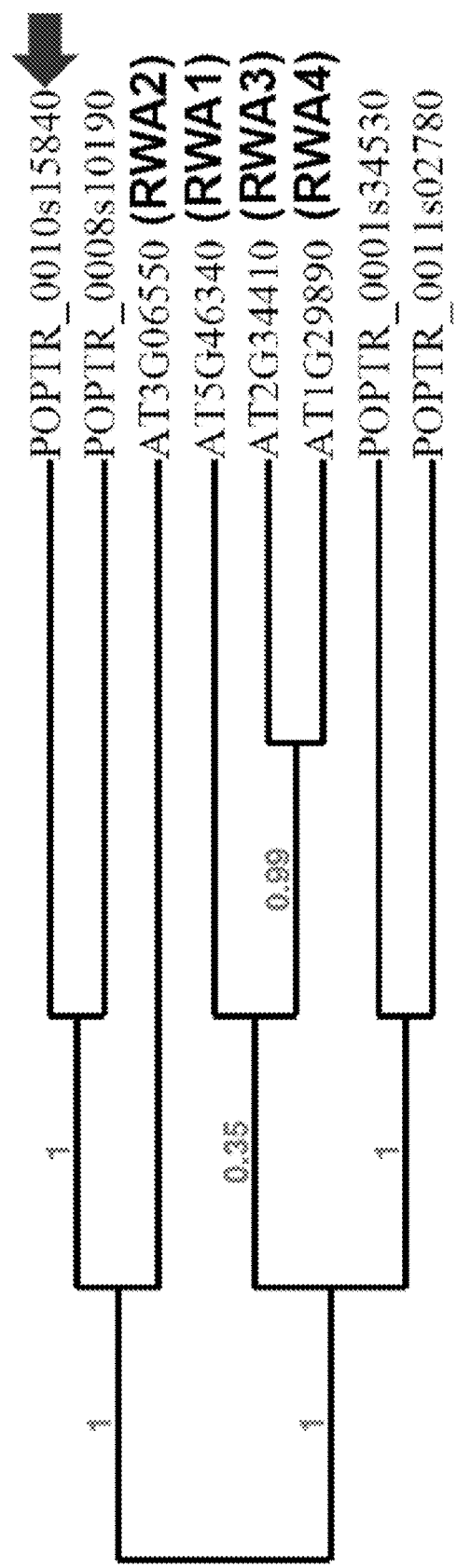
FIG. 2. Phylogenetic analysis of POPTR_0010s15840 and its orthologs in *Arabidopsis*.

As determined by TAIL-PCR, the T-DNA was inserted at a position that is 929 by upstream of the transcription start site of *Populus* gene model POPTR_0010s15840. Quantitative RT-PCR analysis revealed that the transcript level of POPTR_0010s15840 was increased 5.0-fold compared with that in the control plants whereas the transcript level of POPTR_0010s15830, the other gene flanking the same T-DNA insertion site, remained unchanged. These results suggested that the elevated expression of POPTR_0010s15840 is likely responsible for the phenotypes observed in the line E8-33. POPTR_0010s15840 encodes an O-acetyltransferase. POPTR_0010s15840 belongs to a small gene family in *Populus* (FIG. 2), with an orthologous gene in *Arabidopsis* designated as REDUCED WALL ACETYLATION 2 (RWA2).

Figure 3A:
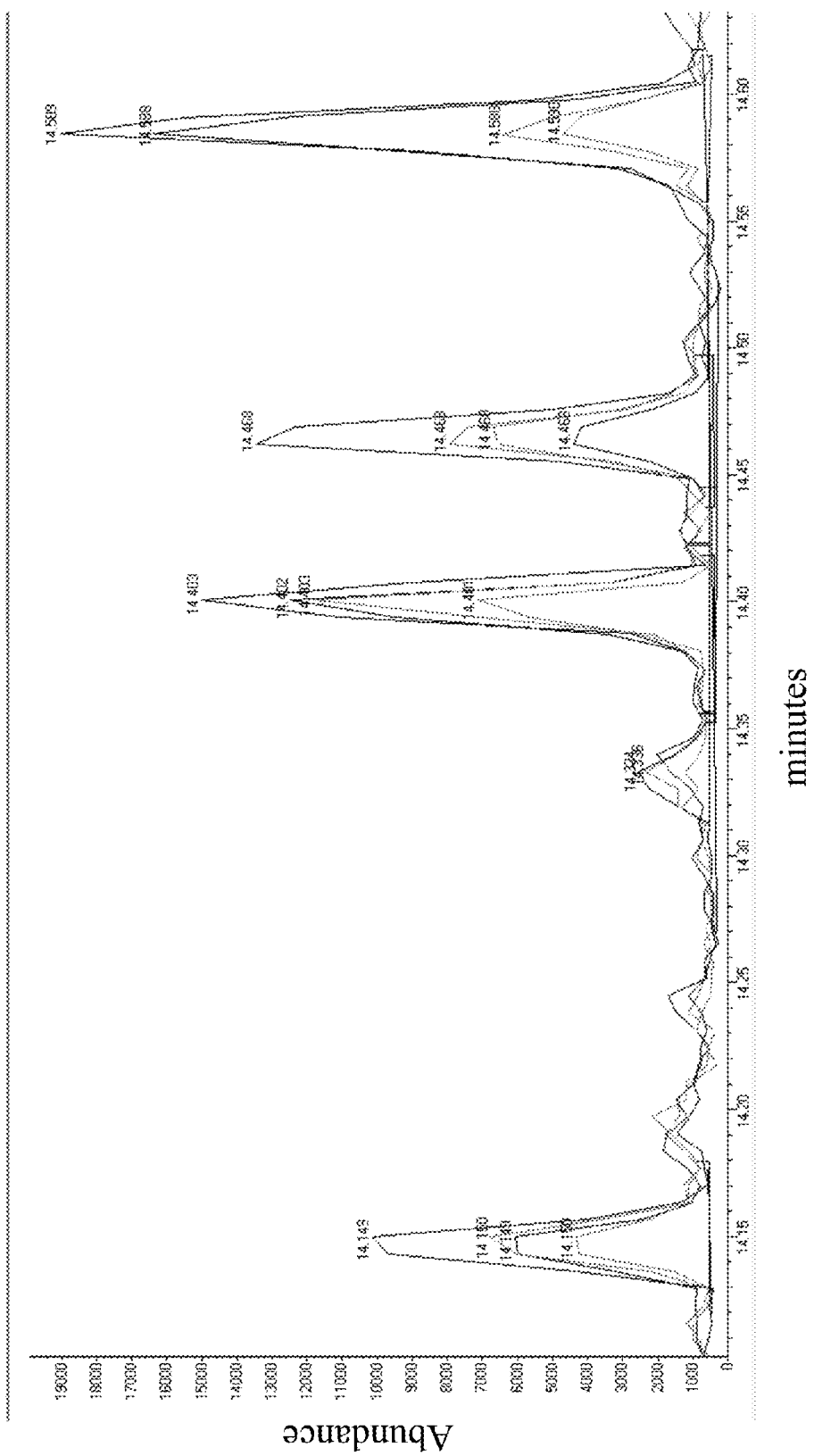
FIGS. 3A-3B. Metabolomic profiling of *Populus* activation tagged lines indicating that an increase in acetylated oligosaccharide in E8-33 correlates with increased acetyltransferase. (A), gas chromatograph (GC) shows a peak at 14.59 minutes that differs between the transgenic plants (E8-33-A and E8-33-C, upper two peaks at 14.59 minutes) and control plants (wild type plants WT-16 and WT-21, lower two peaks at 14.59 minutes). (B), mass spectroscopy (MS) fragmentation pattern of the GC peak at 14.59 minutes showing a peak at 289 m/z for the E8-33 plants indicating an acetylated sugar, sugar acid, or sugar alcohol metabolite, such as a uronic acid or sugar alcohol conjugated to a sugar moiety.
Figure 3B:
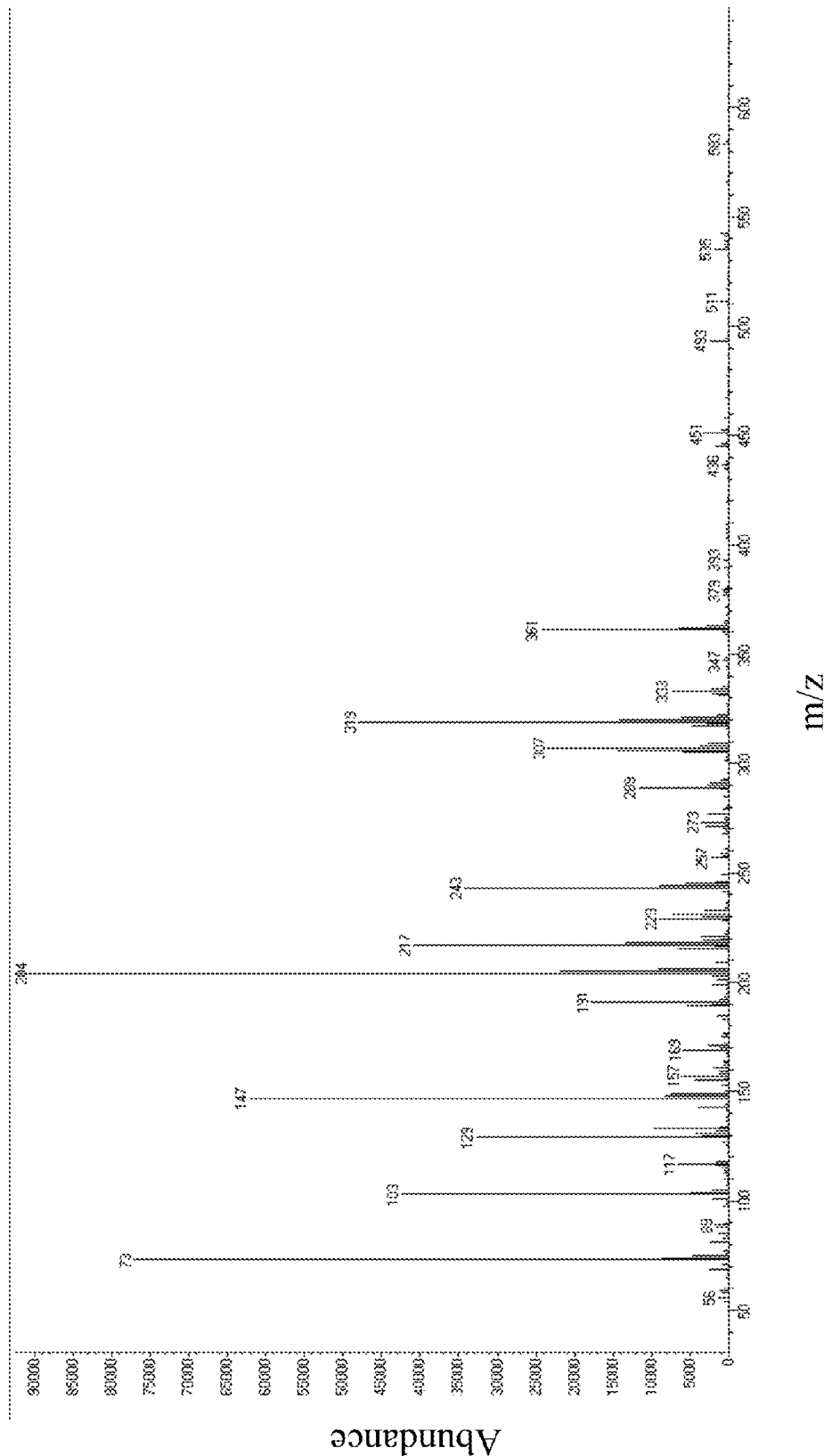

The *Populus* activation tagged line E8-33 was subjected to GC-MS-based metabolomic profiling to determine the downstream impact of gene activation on secondary and small molecules and to correlate the results with the putative function of Gene Y. As described above, available evidence suggested that the elevated expression of O-acetyltransferase is responsible for the high S/G-lignin ratio phenotype observed in the line E8-33. Metabolomic profiling results indicated that acetylated oligosaccharide, specifically acetylated sugar conjugated to an uronic acid or a sugar alcohol is elevated in E8-33 (FIGS. 3A-3B), thus correlating an increase in the expression of acetyltransferase with increased acetylated oligosaccharides and providing further evidence that O-acetyltransferase is responsible for the observed phenotype.

What is claimed is:

1. An expression vector comprising a nucleic acid encoding a protein comprising the amino acid sequence of SEQ ID NO:1, wherein the nucleic acid is operably linked to a heterologous promoter.

2. The expression vector of claim 1, wherein the heterologous promoter is an inducible promoter or a tissue-specific promoter.

3. The expression vector of claim 2, wherein the tissue-specific promoter is a xylem-specific promoter.

4. A transgenic plant transformed with the expression vector of claim 1.

5. The transgenic plant of claim 4, wherein the heterologous promoter is an inducible promoter or a tissue-specific promoter.

6. The transgenic plant of claim 5, wherein the tissue-specific promoter is a xylem-specific promoter.

7. A method of increasing the ratio of syringyl to guaiacyl subunits in a plant; said method comprising the step of transforming the plant with the expression vector of claim 1.

8. The method of claim 7, wherein the heterologous promoter is an inducible promoter or a tissue-specific promoter.

9. The method of claim 8, wherein the tissue-specific promoter is a xylem-specific promoter.

* * * * *

SEQUENCE LISTING

```
<160> NUMBER OF SEQ ID NOS: 2

<210> SEQ ID NO 1
<211> LENGTH: 546
<212> TYPE: PRT
<213> ORGANISM: populus trichocarpa

<400> SEQUENCE: 1

Met Gln Ile Leu Phe Pro Val Thr Arg Gly Gln Phe Ser Phe Leu Leu
1               5                   10                  15

Gly Ile Val Pro Val Phe Ala Ala Trp Ile Tyr Ala Glu Tyr Leu Glu
            20                  25                  30

Tyr Lys Lys Asn Asn Thr Leu Ala Lys Ala Arg His Ser Asp Ile Gly
        35                  40                  45

Leu Val Glu Leu Gly Asn Glu Ala Val Lys Glu Asp Asp Asp Arg Ala
```

-continued

```
                50                  55                  60
Val Leu Leu Glu Gly Gly Gly Leu Gln Pro Ala Ser Pro Lys Ala
 65                  70                  75                  80

Arg Thr Pro Thr Ser Ser Phe Pro Ile Phe Arg Phe Leu Met Met Glu
                     85                  90                  95

Glu Gln Phe Leu Ile Asp Asn Arg Leu Thr Leu Arg Ala Ile Leu Glu
                    100                 105                 110

Phe Gly Phe Phe Met Ala Tyr Phe Tyr Ile Cys Asp Arg Thr Asp Met
                    115                 120                 125

Leu Gly Ser Ser Lys Lys Ser Tyr Asn Arg Asp Leu Phe Leu Phe Leu
                    130                 135                 140

Tyr Phe Leu Leu Ile Ile Val Ser Ala Val Thr Ser Phe Thr Ile His
145                 150                 155                 160

His Asp Lys Ser Pro Phe Ser Gly Lys Pro Ile Leu Tyr Leu Asn Arg
                    165                 170                 175

His Gln Thr Glu Glu Trp Lys Gly Trp Met Gln Val Leu Phe Leu Met
                    180                 185                 190

Tyr His Tyr Phe Ala Ala Thr Glu Ile Tyr Asn Ala Ile Arg Met Phe
            195                 200                 205

Ile Ala Ala Tyr Val Trp Met Thr Gly Phe Gly Asn Phe Ser Tyr Tyr
            210                 215                 220

Tyr Val Arg Lys Asp Phe Ser Leu Ala Arg Phe Ala Gln Met Met Trp
225                 230                 235                 240

Arg Leu Asn Phe Leu Val Leu Phe Cys Cys Val Val Leu Asp Asn Ser
                    245                 250                 255

Tyr Met Leu Tyr Tyr Ile Cys Pro Met His Thr Leu Phe Thr Leu Met
                    260                 265                 270

Val Tyr Ala Ala Leu Gly Ile Phe Asn Lys Tyr Asn Glu Ile Gly Ser
                    275                 280                 285

Val Met Ala Ala Lys Ile Ile Ala Cys Phe Phe Val Val Ile Leu Met
                    290                 295                 300

Trp Glu Ile Pro Gly Val Phe Glu Val Ile Trp Ser Pro Phe Thr Phe
305                 310                 315                 320

Leu Val Gly Tyr Thr Asp Pro Ala Lys Pro Asp Leu Pro Arg Leu His
                    325                 330                 335

Glu Trp His Phe Arg Ser Gly Leu Asp Arg Tyr Ile Trp Ile Ile Gly
                    340                 345                 350

Met Ile Tyr Ala Tyr Tyr His Pro Lys Val Glu Gly Trp Met Glu Lys
                    355                 360                 365

Leu Glu Glu Thr Glu Ala Lys Arg Arg Ile Pro Ile Lys Thr Ala Val
                    370                 375                 380

Ala Thr Ile Ser Leu Ala Val Gly Tyr Thr Trp Tyr Glu Tyr Ile Tyr
385                 390                 395                 400

Lys Leu Asp Lys Ile Ser Tyr Asn Lys Tyr His Pro Tyr Thr Ser Trp
                    405                 410                 415

Ile Pro Ile Thr Val Tyr Ile Cys Leu Arg Asn Val Thr Gln Gln Phe
                    420                 425                 430

Arg Cys Tyr Ser Leu Thr Leu Phe Ala Trp Leu Gly Lys Ile Thr Leu
                    435                 440                 445
```

```
Glu Thr Tyr Ile Ser Gln Ile His Ile Trp Leu Arg Ser Gly Ile Pro
    450                 455                 460

Asp Gly Gln Pro Lys Leu Leu Leu Ser Leu Ile Pro Asp Tyr Pro Met
465                 470                 475                 480

Leu Asn Phe Met Leu Thr Thr Ser Ile Tyr Ile Gly Val Ser Tyr Arg
                485                 490                 495

Leu Phe Asp Leu Thr Asn Thr Leu Lys Thr Ala Phe Val Pro Ser Lys
            500                 505                 510

Asp Asn Lys Arg Leu Thr Asn Asn Ile Ile Thr Ala Ala Ala Val Ser
        515                 520                 525

Ser Val Leu Tyr Ser Leu Ser Phe Val Phe Leu Lys Val Pro Gln Met
530                 535                 540

Leu Val
545

<210> SEQ ID NO 2
<211> LENGTH: 1641
<212> TYPE: DNA
<213> ORGANISM: populus trichocarpa

<400> SEQUENCE: 2
atgcagatct tatttcctgt tactcgcggc cagttttcct ttttgcttgg aatcgtacct      60
gtatttgctg cttggattta cgccgaatat ttggagtaca aaaaaaacaa cccttggcc     120
aaagctaggc attctgatat tggactggtt gaattgggga acgaagcggt taaggaagat    180
gatgatagag ctgttttact cgagggagga ggaggtcttc agcccgcttc tcccaaagct    240
cggactccaa cttcctcatt tcctattttc aggtttctta tgatggaaga gcaattcttg    300
attgataatc ggttgacgct tagagctata ttggaatttg gtttctttat ggcctacttt    360
tacatatgcg accgtactga tatgcttggc tcatctaaga gagttacaa tcgagatctt    420
ttcttgtttc tctacttcct ctcatcata gtttcggcag taacttcttt cacgatacat    480
catgataagt caccgttctc tgggaaacct atactatatt tgaacaggca tcaaaccgag    540
gagtggaaag ctggatgca ggtattattt ttaatgtacc attactttgc tgcgacagaa    600
atatacaatg caatccgcat gtttattgct gcatatgtgt ggatgactgg atttggcaac    660
ttctcatatt attatgttcg caaagatttc agtcttgcaa ggtttgcgca gatgatgtgg    720
cggcttaatt tcctggtgct attctgctgc gttgtactgg acaatagtta catgctatac    780
tatatttgcc ccatgcacac tcttttcact cttatggttt atgcggccct tggtattttc    840
aacaagtaca atgagattgg atcagtcatg gctgcaaaaa ttattgcctg cttctttgtt    900
gttattctca tgtgggaaat tcctggagta tttgaagtga tttggagccc atttactttc    960
cttgttggtt atacggatcc agcaaaacca gatttgcctc gcttgcacga gtggcatttt   1020
cgttctggac ttgatcgcta tatctggata attggaatga tatatgccta ctatcatcca   1080
aaggtggaag gatggatgga gaaactagag gagacagaag cgaagcgcag aataccaatc   1140
aaaacagctg ttgcaacaat atctctggcg gtgggatata catggtacga gtacatatac   1200
aagctggaca agatttctta caacaaatac catccttata cctcatggat tcccataact   1260
gtgtacattt gtttgagaaa tgtcacccag caattccgct gctacagttt gacccttttt   1320
gcatggctag ggaaaatcac cctggagacg tacatttctc aaatccatat ctggttaaga   1380
tcaggcattc cagatggcca accaaaattg ttacttctc taattccaga ctacccaatg   1440
ttgaacttta tgcttaccac atccatatat attggagttt cttacagact cttgatctg   1500
```

```
acaaatacat tgaaaacggc atttgtgccc agcaaagaca ataagcgcct gacaaacaac    1560
ataattacag cagcggcagt ttcaagtgtt ttatattcgc tgtcttttgt attcttaaaa    1620
gtcccgcaga tgctggtttg a                                              1641
```